United States Patent [19]

Hall et al.

[11] Patent Number: 5,650,420
[45] Date of Patent: Jul. 22, 1997

[54] PRAMIPEXOLE AS A NEUROPROTECTIVE AGENT

[75] Inventors: Edward D. Hall, Portage; Philip F. Von Voigtlander, Plainwell, both of Mich.; Frank A. Rohde, Weiler, Germany

[73] Assignees: Pharmacia & Upjohn Company, Kalamazoo, Mich.; Boehringer Ingelheim International GmbH, Weiler, Germany

[21] Appl. No.: 357,121

[22] Filed: Dec. 15, 1994

[51] Int. Cl.$^6$ .................................................. A61K 31/425
[52] U.S. Cl. ................................... 514/367; 514/879
[58] Field of Search ............................ 514/367, 879

[56] References Cited

U.S. PATENT DOCUMENTS 4,843,086  6/1989  Griss et al. ...................... 514/367
4,886,812  12/1989  Griss et al. ...................... 514/321
5,112,842  5/1992  Zierenberg et al. .............. 514/367

FOREIGN PATENT DOCUMENTS 186 087    8/1989  European Pat. Off. .
38 43 227  7/1990  Germany .
WO94/13287 6/1994  WIPO .

OTHER PUBLICATIONS

Society for Neuroscience Abstracts, 19:673 (1993); id., at 1645.

Miya Zawa, et al. Nippon–Yakurigaku–Zasshi 98(6):449–561, (1991).

Ther–Pharmacol–Clin., vol. 11, issue 118, pp. 7–12 (1993).

*Primary Examiner*—Kevin E. Weddington
*Attorney, Agent, or Firm*—Lawrence T. Welch

[57] ABSTRACT

The present invention provides the use of pramipexole as a neuroprotective agent.

3 Claims, No Drawings

PRAMIPEXOLE AS A NEUROPROTECTIVE AGENT

FIELD OF THE INVENTION

The present invention relates to the use of pramipexole or 2-amino-6-n-propylamino-4,5,6,7-tetrahydrobenzo-thiazole or the (−)-enantiomer, thereof and the pharmacologically acceptable salts thereof as a neuroprotective agent.

BACKGROUND OF THE INVENTION

A number of central nervous system diseases and conditions result in neuronal damage. These conditions which can lead to nerve damage include:

Primary neurogenerative disease; Huntington's Chorea; Stroke and other hypoxic or ischemic processes; neurotrauma; metabolically induced neurological damage; sequelae from cerebral seizures; hemorrhagic stroke; secondary neurodegenerative disease (metabolic or toxic); Alzheimer's disease, Senile Dementia of Alzheimer's Type (SDAT); age associated cognitive dysfunctions; or vascular dementia, multi-infarct dementia, Lewy body dementia, or neurogenerative dementia.

Pramipexole is a dopamine-$D_3/D_2$ agonist the synthesis of which is described in European Patent 186 087 and its counterpart, U.S. Pat. No. 4,886,812. It is known primarily for the treatment of schizophrenia and Parkinson's disease. It is known from German patent application DE 38 43 227 that pramipexole lowers the plasma level of prolactin. Also, this European patent application discloses the use of pramipexole in the treatment of drug dependency. Further, it is known from German patent application DE 39 33 738 that pramipexole can be used to decrease abnormal high levels of thyroid stimulating hormone (TSH). U.S. Pat. No. 5,112,842 discloses the transdermal administration of the compounds and transdermal systems containing these active compounds. WO patent application PCT/EP 93/03389 describes the use of pramipexole as an antidepressant agent.

Up to now there is no commercially available drug for the therapeutic treatment of stroke with proven evidence of efficacy.

Surprisingly and unexpectedly, it has been found that pramipexole also has a neuroprotective effect.

INFORMATION DISCLOSURE

Piribedil, a vasodilator which binds to a multitude of receptors including dopamine receptors, is reported to have an effect on functional and biochemical parameters in a gerbil model of ischemia. See, e.g., Society for Neuroscience Abstracts, 19:637 (1993); id., at 1645.

Lisuride binds to several different receptors including dopamine $D_2$ and 5-HT1a receptors. It is reported that Lisuride, when administered before the event, reduced brain edema and prolonged survival time in a rat model of cerebral infarction. Miya Zawa, et al. Nippon-Yakurigaku-Zasshi 98(6):449–561, (1991).

SUMMARY OF THE INVENTION

The present invention particularly provides a method for preventing neuronal damage in a patient suffering from or susceptible to such neuronal damage comprising the administration of an effective amount of pramipexole. By pramipexole is meant 2-amino-6-n-propylamino-4,5,6,7-tetrahydrobenzothiazole, its (−)-enantiomer thereof, and pharmacologically acceptable salts thereof.

Conditions which can cause nerve damage are well-known to an ordinarily skilled neurologist or similar physician and include:

Primary neurogenerative disease;
Huntington's Chorea;
Stroke and other hypoxic or ischemic processes;
Neurotrauma;
Metabolically induced neurological damage;
Sequelae from cerebral seizures;
Hemorrhagic stroke;
Secondary neurodegenerative disease (metabolic or toxic);
Alzheimer's disease, other memory disorders; or
Vascular dementia, multi-infarct dementia, Lewy body dementia, or neurogenerative dementia.

The preferred indication for pramipexole, in the context of the present invention, is Parkinson's disease which is characterized by progressive degeneration of nigrostriatal dopamine neurons. In this sense, the term Parkinson's Disease also comprises the term Parkinson's Syndrome. In addition to pramipexole's palliative action (i.e. replacement of the lost dopamine neurotransmitter function), the compound may slow the degeneration of surviving dopamine neurons and thereby slows the progression of the disease.

The prophylactic use of the compound of this invention includes use as monotherapy in early or pre-symptomatic stages of Parkinson's disease and prevention of neurogenerative disorders base on ischaemia.

The synthesis, formulation and administration of pramipexole is described in U.S. Pat. Nos. 4,843,086; 4,886,812; and 5,112,842; which are incorporated by reference herein.

2-Amino-6-n-propyl-amino-4,5,6,7-tetrahydrobenzothiazole, particularly the (−)-enantiomer thereof, and the pharmacologically acceptable acid addition salts thereof can be given for preventing of neuronal damage. The form of conventional galenic preparations consist essentially of an inert pharmaceutical carrier and an effective dose of the active substance; e.g., plain or coated tablets, capsules, lozenges, powders, solutions, suspensions, emulsions, syrups, suppositories, etc.

The effective dose range is 0.1 to 2.0 mg/kg/day. More preferred is a dose of 1–2 mg/kg/day PO. The preferred total dose level for neuroprotection is 0.5–20 mg/kg/day PO. In addition to being administered by oral or intravenous route, pramipexole may be administered transdermally.

DESCRIPTION OF THE PREFERRED EMBODIMENTS

The present invention is seen more fully by the examples given below:

Example 1

We examined histologically retrograde degeneration of the dopaminergic nigrostriatal (NS) tract over 28 days in gerbils subjected to a 10-minute period of forebrain ischemia via bilateral carotid occlusion. There was in control animals a 39% loss of NS cell bodies in the zona compacta (as judged by tyroxine hydroxylase immunocytochemistry) over that time period. Daily post-ischemic oral dosing (*1 mg/kg PO BID beginning at 1 hr after insult) with pramipexole attenuated 28-day post-ischemic loss of NS DA neurons by 36% (p<0.01 vs vehicle-treated).

Example 2

We have successfully replicated the finding of Example 1; i.e., that pramipexole can protect nigrostriatal dopamine neurons in a gerbil model of 10 minutes of bilateral carotid occlusion-induced forebrain ischemia plus 28 days of post-ischemic survival. The administration of pramipexole was via an initial dose of 1 mg/kg PO 60 minutes after ischemia and again at the end of day 1 followed by twice daily dosing for the next 26 days. A twice daily dose of 0.3 mg/kg produced a threshold effect (14% increase in nigrostriatal dopamine neurons compared to vehicle). A twice daily dose of 1 mg/kg produced a significant 38% improvement in 28 day post-ischemic dopamine neuronal survival (p<0.0001 vs vehicle-treated). This action appears to be specific for dopamine neurons since the post-ischemic loss of the non-dopaminergic neurons in the CA1 area of the hippocampus was not significantly affected.

We claim:

1. A method for preventing neuronal damage in a patient suffering from or susceptible to a condition which can cause such neuronal damage comprising the administration of an 1–20 mg/kg/day by oral administration of pramipexole.

2. A method of claim 1 where the condition is selected from Parkinson's disease, primary neurogenerative disease; Huntington's Chorea; stroke and other hypoxic or ischemic processes; neurotrauma; metabolically induced neurological damage; sequelae from cerebral seizures; hemorrhagic stroke; secondary neurodegenerative disease; Alzheimer's disease, other memory disorders; or vascular dementia, multi-infarct dementia, Lewy body dementia, or neurogenerative dementia.

3. A method of claim 2, where the condition is Parkinson's disease.

* * * * *